United States Patent [19]

Gaughan

[11] Patent Number: 4,487,979
[45] Date of Patent: Dec. 11, 1984

[54] PURIFICATION

[75] Inventor: Roger G. Gaughan, Bartlesville, Okla.

[73] Assignee: Phillips Petroleum Company, Bartlesville, Okla.

[21] Appl. No.: 485,793

[22] Filed: Apr. 18, 1983

[51] Int. Cl.³ ............................................. C07C 35/21
[52] U.S. Cl. .................................. 568/816; 568/819; 568/724
[58] Field of Search ............... 568/724, 810, 816, 822, 568/819

[56] References Cited

U.S. PATENT DOCUMENTS

| | | | |
|---|---|---|---|
| 2,959,622 | 11/1960 | Grimme et al. | 568/724 |
| 3,277,186 | 10/1966 | Robinson et al. | 568/816 |
| 3,673,262 | 6/1972 | Prahl et al. | 568/724 |
| 4,001,343 | 1/1977 | Gaillard et al. | 260/631 H |
| 4,156,098 | 5/1979 | Li | 568/724 |
| 4,240,968 | 12/1980 | Quinn et al. | 568/724 |

OTHER PUBLICATIONS

H. Hopff et al., *Die Makromolekulare Chemic* 91, pp. 121–135 (1966).

A. Terada, *Bulletin of the Chemical Society of Japan*, vol. 39, pp. 2194–2201 (1966).

*Primary Examiner*—Werren B. Lone
*Attorney, Agent, or Firm*—L. M. Lavin

[57] ABSTRACT

The purification of bis(4-hydroxycyclohexyl) alkane, particularly hydrogenated bisphenol A (HBPA) is carried out via recrystallization from at least one halogen-containing solvent solution.

5 Claims, No Drawings

PURIFICATION

BACKGROUND

Hydrogenated bisphenol A (HBPA), also called 2,2-bis(4-hydroxycyclohexyl) propane, is an important reagent in the production of various polymers and engineering plastics. HBPA or its derivatives can be reacted with appropriate acids, amines, etc. to produce, for example, polyesters, polyamides and phenolic polymers. Numerous U.S. patents, e.g. U.S. Pat. Nos. 4,214,040; 4,179,420, 4,102,944; 4,016,112; and 3,956,228, describe the use of HBPA in polyester production alone.

Generally, HBPA-based polymers are produced by reacting a difunctional HBPA-based ingredient with co-reactants having a functionality of two or more. The resultant polymers are linear or cross-linked molecules. Since the co-reactants have two or more sites for reaction, it is important to insure that the presence of monofunctional impurities—which would be chain terminators—is kept at a minimum. Accordingly, it is desirable that monofunctional impurities commonly associated with HBPA, i.e., phenols and mono-hydric alcohols, be removed therefrom before the HBPA is employed to produce polymers.

Additionally, it is well known that the trans, trans isomer of HBPA is more valuable than its other isomers. It has been observed that reaction of the high-melting trans, trans isomer yields polymers having more symmetry and better physical properties, e.g., higher melting points.

INVENTION

It has been discovered that HBPA of high purity and consistent isomer composition can be produced by recrystallization of crude HBPA using halogen-containing alkane solvents.

In a specific embodiment HBPA was recrystallized from chloroform solvent. The recrystallized product was >99% pure. Using gas chromatography, it was determined that the product contained 0.55% cis, cis isomer, 7.85% cis, trans isomer and 91.60% trans, trans isomer.

OBJECTS OF THE INVENTION

It is an object of the invention to purify bis(4-hydroxycyclohexyl) alkanes.

It is another object of this invention to purify hydrogenated bisphenol-A (HBPA).

It is another object of this invention to purify HBPA by recrystallization from certain solvents.

It is a further object to prepare HBPA having high trans, trans isomer content, low content of monofunctional impurities, and good suitability for use in polymerization reactions.

ADVANTAGES

The process of the invention has several advantages over known processes of purifying HBPA. In prior art processes, HBPA has been recrystallized from other solvents to yield products whose melting points indicate that they are not high-purity trans, trans isomeric substances.

A. Terada describes in *Bulletin of the Chemical Society of Japan*, Volume 39 (1966) page 2198, the repeated recrystallization of HBPA from ethyl acetate. H. Hopf et al describe in *Die Makromolekulare Chemie*, 91 (1966), page 124 the repeated recrystallization of HBPA from ethanol/benzene. The disclosures of these publications is hereby incorporated by reference.

As will be shown in the examples of this application, the recrystallization of HBPA from chloroform shows advantages over the recrystallization methods of Terada and Hopf et al. Specifically, the instant process yields HBPA with:

(a) high recovery of purified HBPA,
(b) essentially undetectable impurities, and
(c) consistently high trans, trans isomer content.

Because of consistency of the isomer composition, HBPA made in accordance with the invention can be employed to attain reproducible polymer properties when said HBPA is employed as a monomer in polymerization reactions.

Furthermore, the product's high purity means that there are few, if any, monofunctional impurities, such as monoalcohols, that can act as terminating agents in polymerization reactions and thus inhibit the formation of high molecular weight polymers.

Other advantages and objects of the invention will become apparent from a consideration of the invention's various aspects, as set forth in the following description and claims.

DESCRIPTION OF THE INVENTION

Cyclic Alcohols

The cyclic alcohols to be purified in accordance with the invention are bis(4-hydroxycyclohexyl) alkanes having the general formula:

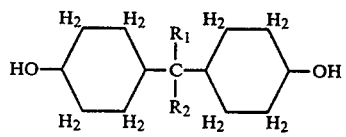

wherein $R_1$ and $R_2$ are independently selected from hydrogen and $C_1$–$C_5$ organic radicals. Preferred $R_1$ and $R_2$ moieties are H, and alkyl radicals such as $CH_3$, $C_2H_5$, $C_3H_7$, $C_4H_9$, $C_5H_{11}$, and the like.

Compounds to be purifed in accordance with the invention include well-known bis(4-hydroxycyclohexyl) alkanes such as:

bis(4-hydroxycycylohexyl) methane, 1,1-bis(4-hydroxycyclohexyl) ethane, 2,2-bis(4-hydroxycyclohexyl) propane, 2,2-bis(4-hydroxycyclohexyl) butane, and the like. A preferred alkane is 2,2-bis(4-hydroxycyclohexyl) propane, also called hydrogenated bisphenol A (HBPA).

Hydrogenated bisphenol A (HBPA) or 2,2 bis(4-hydroxycyclohexyl) propane is most commonly produced by the reaction of bisphenol A with hydrogen. Generally, the presence of one or more conventional hydrogenation catalysts assist the reaction.

Various side reactions occur during the hydrogenation. The by-products formed thereby, i.e., phenol, substituted phenols, cyclohexanol, substituted cyclohexanols and the like, are impurities whose presence with the HBPA hinder the efficiency of subsequent chemical reactions.

The most common techniques for removal of impurities are vacuum distillation and/or recrystallization. Applicant's process for purifying HBPA is essentially a recrystallization technique which employs particular solvents. Other conventional purification methods can be used in combination therewith.

Solvents

The solvent systems from which applicant recovers his product contain halogen-containing organic compounds having significant miscibility with bis(4-hydroxycyclohexyl) alkanes, especially HBPA. Generally, the solvents comprise aliphatic or cycloaliphatic compounds containing from about 1 to about 10 carbon atoms. Preferred solvents are liquid chlorine-containing compounds such as dichloromethane, chloroform, carbon tetrachloride, 1,2-dichloroethane, hexachlorocyclohexane and the like. Mixtures of solvents can be employed.

Highly preferred solvents are chlorine-substituted alkanes, such as the mono- and poly-chlorinated derivations of methane, ethane, propane, butane, cyclobutane, and the like. Solvents used for purifying bis(4-hydroxycyclohexyl) alkanes, especially HBPA include liquid halogen-containing aliphatic and cycloaliphatic compounds containing from about 1 to about 10 C-atoms, such as dichloromethane, chloroform, bromoform, iodoform, carbon tetrachloride, 1,2-dichloroethane, 1,2-dichloropropane, 2,3-dichlorobutane, chlorocyclohexane, hexachlorocyclohexane and the like. Chloroform is highly preferred.

Recrystallization Procedure

The crude HBPA is recrystallized using conventional techniques. While the art is well aware of useful devices and parameters for dissolving, crystallizing, and recovering substances such as HBPA, applicant submits the following as a suggestion from which suitable extrapolation can be made.

The HBPA is mixed with one or more of the inventive solvents with appropriate stirring or agitation. The solvent may be at room temperature or at elevated temperature when it is blended with the crude HBPA. It is preferred that the solvent be heated to a temperature within about 0°–50° C., preferably about 0°–15° C. below its boiling point to aid dissolution. Alternatively, the mixture of HBPA and solvent may be effected without heat, and the mixture subsequently warmed to assist in solution.

The resultant solution is then stirred and filtered using at least one conventional device such as a Buchner funnel, fritted disc, etc.

Following the filtration step, the solution is cooled and the HBPA permitted to solidify in preparation for subsequent recovery and analysis.

Typical techniques for recovering the recrystallized product include filtering, centrifuging, decanting, etc.

EXAMPLES

Example 1

In this example the recrystallization and analysis of 2,2-bis(4-hydroxycyclohexyl) propane is described. 10.90 grams of crude HBPA (containing about 15 weight percent of monohydroxy compounds as impurities; supplied by Rhone Poulenc Chimie Fine, Paris, France) were essentially completely dissolved in 100 mL of boiling chloroform. The solution was cooled to room temperature while stirring and filtered. 2.83 grams of HBPA were recovered in this run (Run 1).

The recrystallized HBPA was analyzed as follows. 40 mg of HBPA was added to 1.0 mL of N,O-bis (trimethyl silyl)trifluoroacetamide (BSTFA) and 1.0 mL of pyridine. After one hour at room temperature the silylation outlined in the 1979/1980 Handbook and General Catalog of the Pierce Chemical Company was complete. The silylated HBPA was introduced into a 5710 A Hewlett-Packard gas chromotograph having an injector temperature of 300° C., a detector temperature of 300° C. and an initial column temperature of 150° C. The sample was left in the gas chromatograph for four minutes before the column temperature was raised at a rate of 16° C. per minute to 200° C. The column was 2 feet long and contained 10% GE SE-30 on 60/80 mesh CP-AW.

The printout of the gas chromatograph showed the monohydroxy impurities first, followed by the geometric isomers of silylated HBPA impurities amounted to essentially 0 weight percent. The isomer content of the recrystallized HBPA was 91.60 percent by weight of trans, trans, 7.85 percent by weight of cis, trans and 0.55 percent by weight of cis,cis.

The melting point of recrystallized HBPA was 184°–186.5° C. This result confirmed that recrystallized HBPA contained chiefly trans, trans-isomer (melting point: 188°–189° C.) and very little cis,trans- and cis,cis-isomers (melting points: 164°–166° C. and 167°–170° C., respectively).

Example II

This example describes the results of the crystallization from three different solvents: chloroform, ethyl acetate and ethanol/benzene (1:1 weight ratio). The recrystallization and analyses were carried out essentially in accordance with the procedure described in Example 1. Results are summarized in Table I.

TABLE I

| Run | Solvent | Solute/Solvent Ratio | Impurities Weight % | Trans,Trans Isomer Weight % | Recovery Weight % |
| --- | --- | --- | --- | --- | --- |
| 1 (Invention) | Chloroform | 10.9 g/100 ml | 0[1] | 91.6 | 26.0 |
| 2 (Invention) | Chloroform | 9.9 g/100 ml | 0[1] | — | 36.5 |
| 3 (Control) | Ethyl Acetate | 8.2 g/100 ml | 0.5[2] | 86.9 | 30.2 |
| 4 (Control) | Ethyl Acetate | 4.9 g/100 ml | 0.5[2] | — | 36.6 |
| 5 (Control) | Ethanol/ Benzene | 10.0 g/50 ml | 0.5[2] | 93.3 | 17.1 |

[1] undetectable
[2] estimated

Data in Table I shows that HBPA recrystallization from chloroform (Runs 1 and 2) according to the process of this invention yielded a purer product at a comparable or higher recovery rate than the recrystallization from the two other solvents (Runs 3, 4, 5). The trans,trans-isomer content of recrystallized HBPA was comparable to that of the two control runs.

Reasonable variations, such as those which would occur to the skilled artisan, may be made herein without departing from the scope of the invention.

I claim:

1. A process for purifying crude bis(4-hydroxycyclohexyl) alkane having the formula

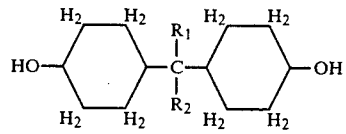

wherein $R_1$ and $R_2$ are independently selected from H, $CH_3$, $C_2H_5$, $C_3H_7$, $C_4H_9$, $C_5H_{11}$, said process comprising recrystallizing said bis(4-hydroxycyclohexyl) alkane from a solvent comprising at least one halogen-containing aliphatic or cycloaliphatic compound containing from about 1 to about 10 carbon atoms.

2. The process of claim 1 werein the bis(4-hydroxycyclohexyl) alkane is hydrogenated bisphenol A.

3. The process of claim 2 wherein the solvent comprises a compound containing chlorine.

4. The process of claim 3 wherein the solvent comprises a chlorinated alkane.

5. The process of claim 4 wherein the solvent contains chloroform.

* * * * *